United States Patent
McNair

(10) Patent No.: US 11,923,048 B1
(45) Date of Patent: *Mar. 5, 2024

(54) DETERMINING MUCOPOLYSACCHARIDOSES AND DECISION SUPPORT TOOL

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 1517 days.

This patent is subject to a terminal disclaimer.

(21) Appl. No.: 16/151,217

(22) Filed: Oct. 3, 2018

Related U.S. Application Data

(60) Provisional application No. 62/567,336, filed on Oct. 3, 2017.

(51) Int. Cl.
| | | |
|---|---|---|
| *G16B 5/00* | (2019.01) | |
| *G01N 33/50* | (2006.01) | |
| *G16B 20/00* | (2019.01) | |
| *G16B 25/00* | (2019.01) | |
| *G16B 40/00* | (2019.01) | |

(52) U.S. Cl.
CPC ........... *G16B 5/00* (2019.02); *G01N 33/5091* (2013.01); *G16B 20/00* (2019.02); *G16B 25/00* (2019.02); *G16B 40/00* (2019.02); *G01N 2800/04* (2013.01); *G01N 2800/50* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,804,405 A | 9/1998 | Ahlfors |
| 6,129,664 A | 10/2000 | Macfarlane et al. |
| 6,759,189 B1 | 7/2004 | Meikle et al. |
| 7,361,481 B2 | 4/2008 | Meikle et al. |
| 7,378,231 B1 | 5/2008 | Meikle et al. |
| 7,662,558 B2 | 2/2010 | Liew |
| 7,951,545 B2 | 5/2011 | Okamura et al. |
| 8,003,337 B2 | 8/2011 | Okamura et al. |
| 8,101,358 B2 | 1/2012 | Liew |
| 8,232,073 B2 | 7/2012 | Crawford et al. |
| 8,410,101 B2 | 4/2013 | Schiffmann et al. |
| 8,569,001 B2 | 10/2013 | Okamura et al. |
| 8,592,140 B2 | 11/2013 | Crawford et al. |
| 8,771,974 B2 | 7/2014 | Crawford et al. |
| 8,809,009 B2 | 8/2014 | Crawford et al. |
| 9,222,120 B2 | 12/2015 | Crawford et al. |
| 9,340,822 B2 | 5/2016 | Crawford et al. |
| 9,495,514 B2 | 11/2016 | McNair |
| 9,495,515 B1 | 11/2016 | Kennedy et al. |
| 11,335,461 B1 | 5/2022 | Mcnair |
| 2006/0172429 A1 | 8/2006 | Nilsson et al. |
| 2007/0077553 A1 | 4/2007 | Bentwich |
| 2007/0118410 A1 | 5/2007 | Nadai |
| 2008/0056994 A1 | 3/2008 | Kaneski et al. |
| 2009/0299645 A1 | 12/2009 | Colby et al. |
| 2010/0047844 A1 | 2/2010 | Aerts |
| 2010/0062948 A1 | 3/2010 | Kleinfeld et al. |
| 2011/0093249 A1 | 4/2011 | Holmes et al. |
| 2011/0212090 A1 | 9/2011 | Pedersen et al. |
| 2013/0287772 A1 | 10/2013 | Halbert et al. |
| 2013/0304392 A1 | 11/2013 | Deciu et al. |
| 2015/0005189 A1 | 1/2015 | Wong et al. |
| 2016/0178643 A1 | 6/2016 | Everett et al. |
| 2018/0068083 A1 | 3/2018 | Cohen et al. |
| 2019/0086324 A1 | 3/2019 | Marrinucci et al. |
| 2021/0110895 A1 | 4/2021 | Shriberg et al. |
| 2021/0319899 A1 | 10/2021 | Liu et al. |
| 2021/0353224 A1 | 11/2021 | Etkin et al. |

(Continued)

FOREIGN PATENT DOCUMENTS

| | | |
|---|---|---|
| EP | 2024745 A2 | 2/2009 |
| EP | 2365458 A2 | 9/2011 |

(Continued)

OTHER PUBLICATIONS

Sharma, Gulshan B., et al. "Machine learning based analytics of micro-MRI trabecular bone microarchitecture and texture in type 1 Gaucher disease." Journal of Biomechanics 49.9 (2016): 1961-1968.*
Wikipedia, "Support Vector Machine," URL (https://en.wikipedia.org/wiki/Support_vector_machine), 13 pages, downloaded Jun. 26, 2023.*
Non-Final Office Action received for U.S. Appl. No. 15/913,663, dated Jul. 16, 2021, 18 pages.
Notice of Allowance received for U.S. Appl. No. 15/913,663, dated Jan. 12, 2022, 8 pages.
Aerts et al., "Biomarkers in the diagnosis of lysosomal storage disorders: proteins, lipids, and inhibodies", Journal of Inherited Metabolic Disease, vol. 34: 605-619, Available online at: <https://doi.org/10.1007/s10545-011-9308-6>, Mar. 29, 2011, pp. 605-619.

(Continued)

*Primary Examiner* — G. Steven Vanni
(74) *Attorney, Agent, or Firm* — Invoke

(57) ABSTRACT

A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable-composite-biomarker comprising a specific set of physiological variables of the patient. This multi-variable statistical predictive biomarker approach may be employed for identifying persons whose attributes are consistent with features or lysosomal storage diseases, such as attenuated mucopolysaccharidosis Type 1 (Hurler-Scheie or Scheie syndromes).

22 Claims, 8 Drawing Sheets

(56) References Cited

U.S. PATENT DOCUMENTS

2021/0358594 A1 11/2021 Mellem et al.
2021/0383924 A1 12/2021 Rajan et al.

FOREIGN PATENT DOCUMENTS

JP 2015-230199 A 12/2015
WO 2016/012864 A2 1/2016

OTHER PUBLICATIONS

Non-Final Office Action received for U.S. Appl. No. 15/913,663, dated Jan. 31, 2020, 16 pages.
Berk et al., "Studies of Bilirubin Kinetics in Normal Adults", Journal of Clinical Investigation, vol. 48, 1969, pp. 2176-2190.
Bhutani et al., "Predictive Ability of a Predischarge Hour-Specific Serum Bilirubin for Subsequent Significant Hyperbilirubinemia in Healthy Term and Near-Term Newborns", Pediatrics, vol. 103, No. 1, Jan. 1999, pp. 6-14.
Bjerre et al., "Surveillance Extreme Hypebilirubinaemia in Denmark. A Method to Identify the Newborn Infants", Acta Paediatrica, vol. 97, 2008, pp. 1030-1034.
Boo et al., "Prediction of Severe Hyperbilirubinaemia Using the Bilicheck Transcutaneous Bilirubinometer", Journal of Pediatrics and Child Health, vol. 43, 2007, pp. 297-302.
Dennery et al., "Neonatal Blue-Light Phototherapy Could Increase the Risk of Dysplastic Nevus Development", Pediatrics, vol. 120, No. 1, 2007, pp. 247-248.
Dennery et al., "Neonatal Hyperbilirubinemia", The New England Journal of Medicine, vol. 334, No. 8, Feb. 2001, pp. 581-590.
Dennery, Phyllis A., "Pharmacological Interventions for the Treatment of Neonatal Jaundice", Seminars in Neonatology, vol. 7, 2002, pp. 111-119.
Facchini et al., "Follow-Up of Neonatal Jaundice in Term and Late Premature Newborns", Jornal de Pediatria, vol. 33, No. 4, 2007, pp. 313-318.
Gartner et al., "Jaundice and Breastfeeding", Pediatric Clinics of North America, vol. 48, No. 2, Apr. 2001, pp. 389-399.
Gillespie et al., "One Size Does Not Fit All: Interpreting Laboratoty Data in Pediatric Patients", AMIA 2003 Symposium Proceedings, 2003, p. 850.
Gloria-Bottini et al., "ADA Genetic Polymorphism and the Effect of Smoking on Neonatal Bilirubinemia and Developmental Parameters", Early Human Development, vol. 11, 2008, pp. 739-743.
Huang et al., "Risk Factors for Sever Hyperbilirubinemia in Neonates", Pediatric Research, vol. 56, No. 5, 2004, pp. 682-689.
Ivanciuc, Ovidiu, "Applications of Support Vector Machines in Chemistry", Reviews in Computational Chemistry, vol. 23, 2007, pp. 291-400.
Jangaard et al., "Outcomes in a Population of Healthy Term and Near-Term Infants With Serum Bilirubin Levels of >Or=325 Micromol/L (>Or=19 mg/dL) Who Were Born in Nova Scotia, Canada, Between 1994 and 2000", Pediatrics, vol. 122, No. 1, Jul. 2008, pp. 119-124.
Kaplan et al., "Evaluation of Discharge Management in the Prediction of Hyperbilirubinemia: The Jerusalem Experience", The Journal of Pediatrics, vol. 150, 2007, pp. 412-417.
Keren et al., "A Comparison of Alternative Risk-Assessment for Predicting Significant Neonatal Hyperbilirubinemia in Terms and Near-Term Infants", Pediatrics, vol. 121, No. 1, Jan. 2008, pp. e170-e179.
Kuzniewicz et al., "Risk Factors for Severe Hyperbilirubinemia Among Infants with Borderline Bilirubin Levels: A Nested Case-Control Study", The Journal of Pediatrics, vol. 153, 2008, pp. 234-240.
"Management of Hyperbilirubinemia in the Newborn Infant 35 or More Weeks of Gestation", Pediatrics, vol. 114, Jul. 2004, pp. 297-316.
Moerschel et al., "A Practical Approach to Neonatal Jaundice", American Family Physician, vol. 77, No. 9, May 2008, pp. 1255-1262.
Ostrow et al., "Phototherapy for Neonatal Jaundice", The New England Journal of Medicine, vol. 358, No. 23, 2008, pp. 2524-2525.
Petrone et al., "Early Hospital Discharge of the Healthy Term Neonate: The Italian Perspective", Minerva Pediatrica, vol. 60, No. 3, 2008, pp. 273-276.
Setia et al., "Neonatal Jaundice in Asian, White, and Mixed-Race Infants", Archives of Pediatrics and Adolescent Medicine, vol. 156, No. 3, Mar. 2002, pp. 276-279.
Shortland et al., "Understanding Neonatal Jaundice; U.K Practice and International Profile", The journal of the Royal Society for the Promotion of Health, vol. 128, No. 4, Jul. 2008, pp. 202-206.
Zanardo et al., "Cytokines in Human Clostrum and Neonatal Jaundice", Pediatric Research, vol. 62, No. 2, 2007, pp. 191-194.
Final Office Action received for U.S. Appl. No. 15/913,663, dated Jul. 21, 2020, 18 pages.
Pre-Interview First Office action received for U.S. Appl. No. 15/912,258, dated May 11, 2022, 4 pages.
Patel et al., "Cardiovascular Events in Patients With Fabry Disease: Natural History Data From The Fabry Registry", Journal of the American College of Cardiology 57.9, 2011, pp. 1093-1099.
Ramaswami et al., "Measuring Patient Experiences in Fabry Disease: Validation of the Fabry-specific Pediatric Health and Pain Questionnaire (Fphpq)", Health and Quality of Life Outcomes 10.1; Available online at :<http://www.hqlo.com/content/10/1/116>, 2012, pp. 1-9.
Rozenfeld, Paulaa. , "Fabry Disease: Treatment and Diagnosis", IUBMB life 61.11; DOI: 10.1002/ iub.257, 2009, pp. 1043-1050.
Weidemann et al., "The Variation of Morphological and Functional Cardiac Manifestation in Fabry Disease: Potential Implications for the Time Course of the Disease", European heart journal 26.12; doi: 10.1093/eurheartj/ehi143, 2005, pp. 1221-1227.

* cited by examiner

EXAMPLE APPLICATION USER INTERFACE

Patient aged between 0 and 40 years... | enter
---|---
Joint pain or stiffness? (Y/N) [ICD-9: 719.4x, 719.5x, ICD-10: M25.xx, M26.xx] | Y
Two or more of the listed comorbid conditions*? (Y/N) | N
hsCRP > 2.8 mg/L? (Y/N) | Y
RDW > 16.1 μm? (Y/N) | Y
RBC sedimentation rate > 10 mm/hr? (Y/N) | Y
MPV > 9.4 fL? (Y/N) | Y
AST > 38 U/L? (Y/N) | Y
ALKP > 180 U/L? (Y/N) | Y
FVC% or FEV1% < 70%? (Y/N) | Y

310 evaluate | results
---|---
data complete? | Yes
Likelihood of attenuated MPI-I meriting further testing... | Moderate to High

320

330 — 2%   332 — ( 0%  to  18% ) — 336

**\* Comorbid conditions** | ICD-9 | | ICD-10 |
---|---|---|---|---
Scoliosis or kyphosis | 737.xx | | M40.xx | M41.xx
Dysostosis | 754.xx | - 756.xx | Q65.xx | - Q79.xx
Genu valgum | 736.41 | | M21.069 | Q68.2
Pes cavus | 754.71 | | Q66.7 |
Joint contracture(s) | 718.4x | | M24.50 |
Hepatomegaly or splenomegaly | 789.1 | 789.2 | R16.0 | R16.1
Hearing loss/use of hearing aids | 389.xx | | H90.xxx |
Respiratory tract infections or community acquired pneumonia, recurrent | 486.xx | V12.61 | J18.xx | Z87.01
Sleep apnea/noisy nighttime breathing | 327.20 | 327.23 | G47.3x |

```
###########################################################################

# Bayesian logistic regression model for small ICD-10 attenuated MPS-I dataset

##################################################################### library(mcmc)

mps1 <- read.csv(file="c:/0_cerdsm/IP/orphan_MPS_I/dsm_mps1.csv", header=TRUE,
         colClasses=c("character",rep("integer",9),"numeric","factor"))
# pat,joint,comor,crp,rdw,sed,ast,mpv,alkp,fev1fvc,score,mps1
mps1 <- mps1[,-1]

# conventional logistic regression does not converge for so small and near-singular a dataset
# fit <- glm(mps1 ~ ., data=mps1, family=binomial(link=logit), epsilon=1e-4, maxit=100)
out <- glm(mps1 ~ score, data=mps1, family=binomial(), x=TRUE)

x <- out$x
y <- out$y
lupost <- function(beta, x, y) {
  eta <- as.numeric(x %*% beta)
  logp <- ifelse(eta < 0, eta - log1p(exp(eta)), - log1p(exp(- eta)))
  logq <- ifelse(eta < 0, - log1p(exp(eta)), - eta - log1p(exp(- eta)))
  logl <- sum(logp[y == 1]) + sum(logq[y == 0])
  return(logl - sum(beta^2) / 8)
} set.seed(42)
beta.init <- as.numeric(coefficients(out))
out <- metrop(lupost, beta.init, 1e3, x=x, y=y)
out <- metrop(out, scale=0.7, x=x, y=y)
out$accept
out <- metrop(out, nbatch=1e4, x=x, y=y)
out$accept str(out)
List of 13
# $ accept   : num 0.395
# $ batch    : num [1:10000, 1:2] -3.63 -3.63 -3.63 -3.65 -3.65 ...
# $ initial  : num [1:2] -3.35 2.03
# $ final    : num [1:2] -3.45 2.21
```

*FIG. 5*

```
library(pROC)

ds4 <- read.csv(file="c:/0_cerdsm/IP/orphan_MPS_I/roc.csv")
roc1 <- roc(ds4[,1] ~ ds4[,2], percent=TRUE,
# arguments for auc
# partial.auc=c(100, 90), partial.auc.correct=TRUE,
#   partial.auc.focus="sens",
# arguments for ci
  ci=TRUE, boot.n=100, ci.alpha=0.9, stratified=FALSE,
# arguments for plot
#   auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)

# column-major
dsm <- matrix(c(43,2,1,54), ncol=2)
fisher.test(dsm)
p-value < 2.2e-16 odds ratio
848.1562 prevalence 45%
sens 96% (92 - 100)
# spec 98% (96 - 100)
# PPV 98% (95 - 100)
# NPV 96 (93 - 100)
# chisquare 84.5
```

*FIG. 6*

DETERMINING MUCOPOLYSACCHARIDOSES AND DECISION SUPPORT TOOL

CROSS-REFERENCE TO RELATED APPLICATIONS

This application claims the benefit of U.S. Provisional Application No. 62/567,336, entitled "Determining Mucopolysaccharidoses and Decision Support Tool," filed Oct. 3, 2017, which is expressly incorporated by reference in its entirety.

BACKGROUND

Lysosomal storage disorders are relatively rare inherited conditions involving enzyme deficiencies that can impair the functioning of many body organ systems by the accumulation of abnormal amounts of molecules in the lysosome organelles of the body's cells, usually producing severe disability and shortened life-expectancy. Effective treatments are available for some such disorders and may involve enzyme replacement therapy (ERT) involving ongoing periodic infusions of a synthetic recombinant version of the enzyme that is deficient, or stem cell transplantation, or other treatment modalities. Patients who have certain inherited lysosomal storage disorders, such as mucopolysaccharidoses, have widely varied clinical courses and presentations. Symptoms are typically first experienced in childhood and can be misinterpreted by physicians and other clinicians. Most patients generally experience a period of normal development followed by a decline in physical and/or mental function. Decline, once it has commenced, is generally not reversible. Signs and symptoms of the disease usually increase in number and severity as an individual ages. Variations in the presenting signs and symptoms are so diverse as to pose significant diagnostic challenges for most clinicians. The comparative rarity of lysosomal storage diseases, such as less-severe or "attenuated" mucopolysaccharidosis Type 1 (MPS-I), means that most clinicians might never encounter a single patient having such a disorder in their entire clinical career. As a result, many patients having such conditions may go years undiagnosed or, alternatively, are misdiagnosed and are treated for many years on the basis of an incorrect diagnosis. Such erroneous misdiagnosis-based treatments (or non-treatments) are ineffective or even unsafe and impair the health of the patient or lead to needless progression of the disease or irreversible loss of body function.

Mucopolysaccharidoses are autosomal-recessive lysosomal storage disorders caused by an absence of, or insufficient activity of or levels of, the enzyme alpha-L-iduronidase. Prevalence is approximately 1:100,000. Iduronidase deficiency or dysfunction results in accumulation of large amounts of mucopolysaccharides in the cells, interfering with the cells' functioning.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter. A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable composite-biomarker comprising a specific set of physiological variables of the patient. This multi-variable statistical predictive biomarker approach may be employed for identifying persons whose attributes are consistent with features of lysosomal storage diseases, such as attenuated mucopolysaccharidosis Type 1 (Hurler-Scheie or Scheie syndromes).

In embodiments, a multi-variable logistic regression statistical model capable of calculating a probability of a lysosomal storage disease is generated. Using an input data set for a patient and the multi-variable logistic regression statistical model, a probability of a lysosomal storage disease is determined and presented to a clinician to guide decision-making regarding additional diagnostic or prognostic evaluation. Moreover, some embodiments further comprise technologies for scoring or ascertaining the severity of a previously-diagnosed lysosomal storage disease condition in human patients, such as attenuated MPS-I disease, to assist in optimizing the medical treatment of individual patients and as a biomarker to follow the efficacy of treatment in animal models and in patients.

Based on this determined result (which may include one or more of a prediction, scoring, and/or severity), one or more actions may be carried out automatically or may be recommended, such as, without limitation, generating notifications such as electronic messages or alarms, based on the probability or score which may be emitted or otherwise provided to the caregiver and/or to the patient, advising them of the probability of an inherited lysosomal storage disease meriting further diagnostic testing. In some embodiments, recommendations for specialist caregivers may be generated (or appointments may be automatically generated) and/or one or more EHR transactions may be automatically triggered by the determined result or score so as to initiate said diagnostic testing procedures. Some embodiments integrate with other decision support tools and related tools, such as Cerner Millennium orders, Discern Expert CDS, iView, or similar applications.

BRIEF DESCRIPTION OF THE DRAWINGS

The present technology is described in detail below with reference to the attached drawing figures, wherein:

FIG. 3 depicts an example graphical user interface of a multivariable predictive model component of a decision-support tool for predicting a lysosomal storage diseases in a human patient, in accordance with an embodiment of the disclosure;

FIG. 5 illustratively provides an example embodiment of a computer program routine for predicting a lysosomal storage diseases in accordance with an embodiment of this disclosure and further described in connection to FIG. 2B; and FIG. 6 illustratively provides an example embodiment of a computer program routine for evaluating performance of an example embodiment reduced to practice and generating the ROC of FIG. 4A.

DETAILED DESCRIPTION

Figure 1A:
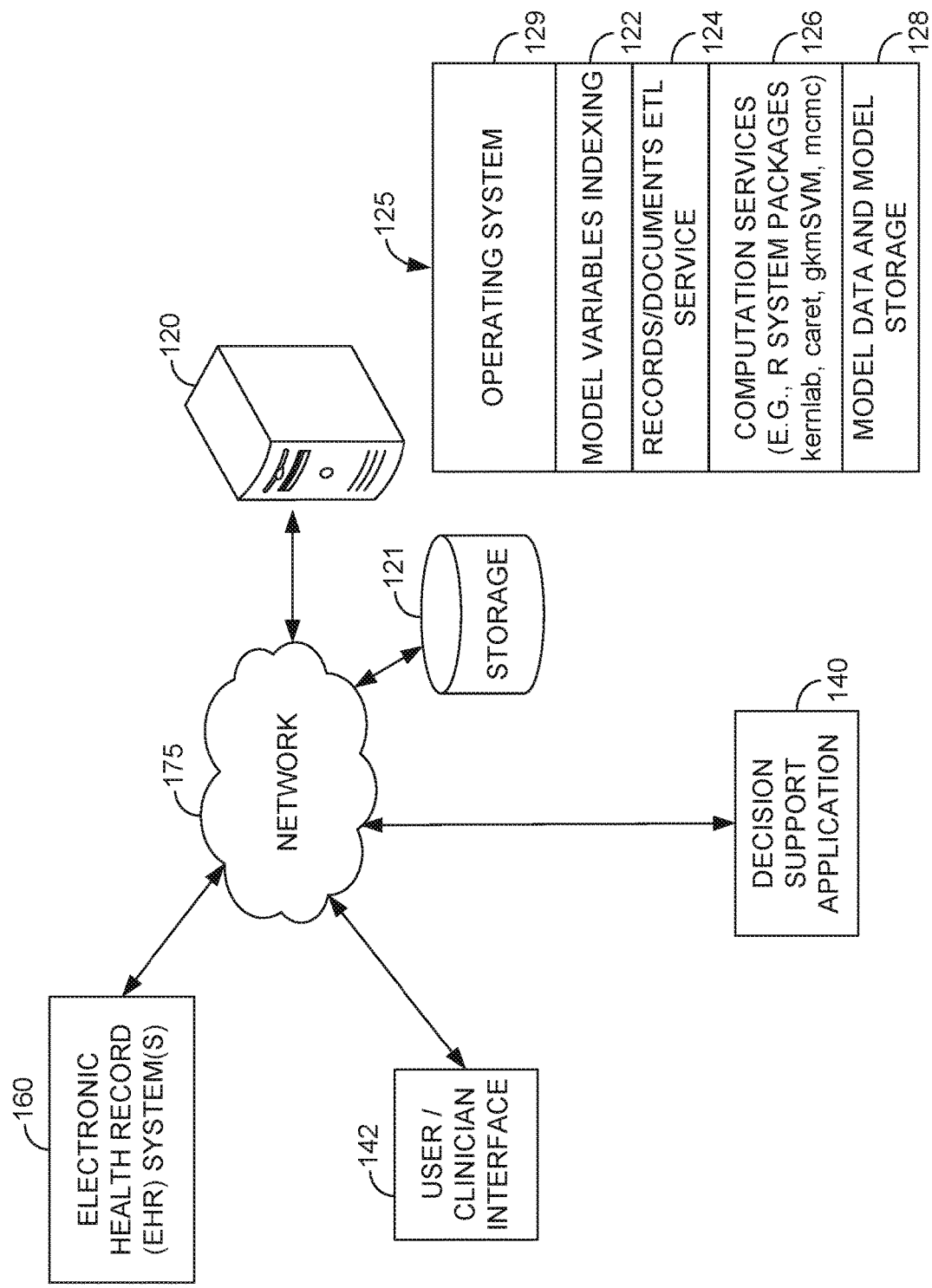
FIGS. 1A and 1B depict aspects of an illustrative architecture suitable for practicing an embodiment of the technology.

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our technology may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

Aspects of the technology described herein may be utilized for a screening procedure and multi-variable logistic regression based biomarker, which determines a numerical probability of a lysosomal storage disease condition, such as attenuated MPS-I disease. Such technology is particularly valuable for patients in whom other diagnostic and prognostic means tend to yield excessive false-negative results. In particular, we determined that increased red blood cell size distribution width (RDW), elevated aminotransferase and alkaline phosphatase enzyme levels, elevated C-reactive protein levels and erythrocyte sedimentation rate, and significant relative decreases in respiratory forced expiratory volume and/or forced vital capacity were identified as strongly statistically associated with a diagnosis of attenuated MPS-I disease. We have also determined that a tendency toward mild to moderate platelet macrocytosis, even in the absence of clinically significant platelet turnover, was also identified and may indicate increased destruction of platelets in the reticuloendothelial system as part of the active processes in lysosomal storage diseases. Utilizing our findings, which have not previously been reported in the known research literature, we developed a multi-variable composite biomarker pattern and predictive model, which we integrated into a decision-support system. In some embodiments, a decision support tool is provided, which may be a component in an electronic health records (EHR) system for detecting presence, identity, and/or severity of a lysosomal storage disorder in patients, for notifying caregivers, and/or generating a recommendation or automatically performing additional actions such as scheduling diagnostic testing, treatments, modification to care plans, or other intervening actions. For example, one embodiment comprises generating a notification indicating a patient's probability or severity of a lysosomal storage disorder.

According to one embodiment, as will be further described herein, systems and computerized methods are provided for determining the presence, identity, and/or severity of a lysosomal storage disease or condition in an individual, where the disease or condition is associated with the accumulation of abnormal amounts of molecules in the lysosome organelles of the body's cells, usually producing severe disability and shortened life-expectancy. In some embodiments, these systems or methods are incorporated into a decision support tool used for screening, monitoring, and/or treating a patient. The decision support tool may utilize a multi-variable composite biomarker pattern and predictive model. In one embodiment, the predictive model comprises a logistic regression model. In one embodiment, the biomarker patterns comprise a set or pattern of physiological variables (which may also include clinical variables comprising conditions or clinical events) associated with a particular patient, which operate as independent variables referenced in the predictive model. In some embodiments, these physiological variables include: attribution of arthralgia; attribution of a plurality of conditions including: scoliosis or kyphosis, dysostosis, genu valgum, pes cavus, joint contracture, hepatomegaly or splenomegaly, hearing loss/use of hearing aids, recurrent respiratory tract infections or community acquired pneumonia, and sleep apnea/noisy nighttime breathing as a composite variable; elevated C-reactive protein; elevated erythrocyte sedimentation rate; increased red blood cell size distribution width (RDW); elevated aminotransferases; elevated alkaline phosphatase; platelet macrocytosis; and relative decrease in forced expiratory volume and/or forced vital capacity.

Based on the multi-variable composite biomarker pattern, a predictive model and model coefficients are instantiated. A patient is identified and EHR information for the patient is accessed. The EHR information may include demographic, diagnostic, and laboratory information about the patient. Inputs for variable values corresponding to the biomarker pattern are received from the patient's EHR, and a probability is determined from the model. In some embodiments, the determined probability may be considered a score denoting the likelihood of the patient's having a lysosomal storage disease or condition.

Next, the determined probability or score is compared to one or more thresholds for lysosomal storage disorder diagnostics. In some embodiments, based on the comparison, one or more risk levels are determined associated with the probability or severity of a lysosomal storage disorder in the patient. Based on the comparison to the one or more thresholds, if the threshold(s) are not exceeded, then routine care for the patient may be carried out, as clinically indicated. But where the one or more thresholds are satisfied, then one or more intervening actions may be invoked. The one or more actions may be based on the determined probability or score satisfying the threshold(s) or the specific value of the determined probability or score. In some embodiments, an explanatory analysis may be prepared to accompany the model for the significant values and deviations. Further, in some embodiments, an application and graphical user interface are provided for displaying a probability result or score denoting the likelihood of the patient having a lysosomal storage disease or condition.

As described above, due to the rarity of lysosomal storage diseases, such as less-severe or "attenuated" mucopolysaccharidosis Type 1 (MPS-I), many clinicians might never encounter a single patient having such a disorder in their entire clinical career, and many patients having such conditions may go years undiagnosed or may be misdiagnosed, and may be treated for many years on the basis of an incorrect diagnosis. Such erroneous misdiagnosis-based treatments (or non-treatments) are ineffective or even unsafe, and impair the health of the patient or lead to needless progression of the disease or irreversible loss of body function. In particular, conventional approaches to detecting this condition often entail measuring lysosomal enzyme levels or other specific gene products, or levels of mucopolysaccharide-related compounds that result from the presence of or deficiencies in the enzyme activity of enzymes related to mucopolysaccharide metabolism. Yet other conventional approaches entail genotyping or sequencing, or other genomics or proteomics testing. Some of these methodologies involve invasive means, such as electromyography or tissue biopsy or other surgical procedures, and many of these conventional approaches are not widely available.

Moreover, these conventional approaches involve expensive, time-consuming tests and are therefore neither practical nor suitable to utilize for the purposes of screening large numbers of prospective patients for possible lysosomal storage disorders. In contrast, embodiments of technology described herein solves these problems by providing a convenient, rapid, and inexpensive screening system and method that relies upon information that may already have been determined in the course of providing routine care and diagnostic testing or that, at most, requires limited additional measurements that are widely available in most health facilities. For example, if the probability or risk of a lysosomal storage disease or condition that is predicted by an embodiment of this technology exceeds a threshold, then an electronic communication with the attending clinician may be generated and one or more EHR transactions may be initiated, such that diagnostic interventions (including more expensive, or time-consuming testing) capable of ruling-in or ruling-out the lysosomal storage disease or condition are undertaken. Accordingly, embodiments of this technology may be utilized as a screening means to afford timely, accurate, and cost-effective definitive diagnosis in a substantially larger cohort of persons at-risk than has heretofore been practical.

The present technology further improves the EHR system itself and utilizes the EHR system in a manner that is not well-understood, routine, and conventional in the field. Conventional EMR system tend to act as a passive repository for data, collecting and storing health information about patients. However, the EMR system itself is not generally utilized to actively diagnose and treat patients. The discovery that certain variables may be used for predicting and diagnosing lysosomal storage diseases enables the EMR to be utilized, not only as a passive data repository, but also as an active diagnostic and predictive tool for lysosomal storage diseases. Because the EMR system was previously unable to be used in such manners, the methods and technology provided by this disclosure enable new uses for the EMR system, thereby improving the underlying technology of the EMR system. Additionally, as noted, conventional EMR systems are used as passive data repository. The technology provided by this disclosure, however, utilizes the EMR system as an active diagnostic and predictive tool. Using EMR systems in this manner is not a well-understood, routine, or conventional use of such systems in the field.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the described technology. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections, or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the technologies described herein, sequence itemset mining is performed using data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, or in-home patient monitors or sensors, for example.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of manager application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients having a lysosomal storage disorder. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical or psychiatric caregiver or the like) to a score or prediction determined according to the technologies described herein, including information indicating a likelihood that a patient has a lysosomal disorder, the severity of the disorder, and/or additional classification of the disorder, such as the likelihood of a specific condition (e.g., a lysosomal storage disease condition such as attenuated MPS-I disease). One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined probability or score, recommendations, scheduling orders, providing instructions, or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for providing diagnostic services or evaluation of the performance of various embodiments. One example embodiment of a user/clinician interface 142 and decision support application 140, which is actually reduced to practice is illustratively provided in FIG. 3, which is further described below.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing service 122 and records/documents ETL service 124 provide services that facilitate retrieving patient physiological variables, which may include frequent item sets, extracting database records, and cleaning the values of variables in records. For example, services 122 and/or 124 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages kernlab, for kernel-based machine learning classification, regression, clustering, and dimensionality reduction methods; caret, for training classification and regression models; gkmSVM, for implementing a Gapped-Kmer Support Vector Machine; and mcmc, for Markov Chain Monte Carlo operations. Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 5 and 6. Computation services 126 also may include services or routines for utilizing one or more prediction, forecasting, or diagnostic models, such as the models described in connection to FIGS. 2A and 2B and the example computer program routines illustratively provided in FIGS. 5 and 6. In some embodiments, computation services 126 use EHR system(s) 160, model data and model storage services 128, and/or other components of example operating environment 100, and may also include services to facilitate receiving and/or pre-processing physiological data. Model data and model storage services 128 may be utilized to perform services for facilitating storage, retrieval, and implementation of the models described herein and of the data used in the models.

Some embodiments of stack 125 may further comprise services for utilizing an Apache Hadoop and Hbase framework (not shown), or similar frameworks operable for providing a distributed file system, and which in some embodiments facilitate access to cloud-based services such as those provided by Cerner Healthe Intent®. Additionally, some embodiments of stack 125 may further comprise one or more services, such as stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
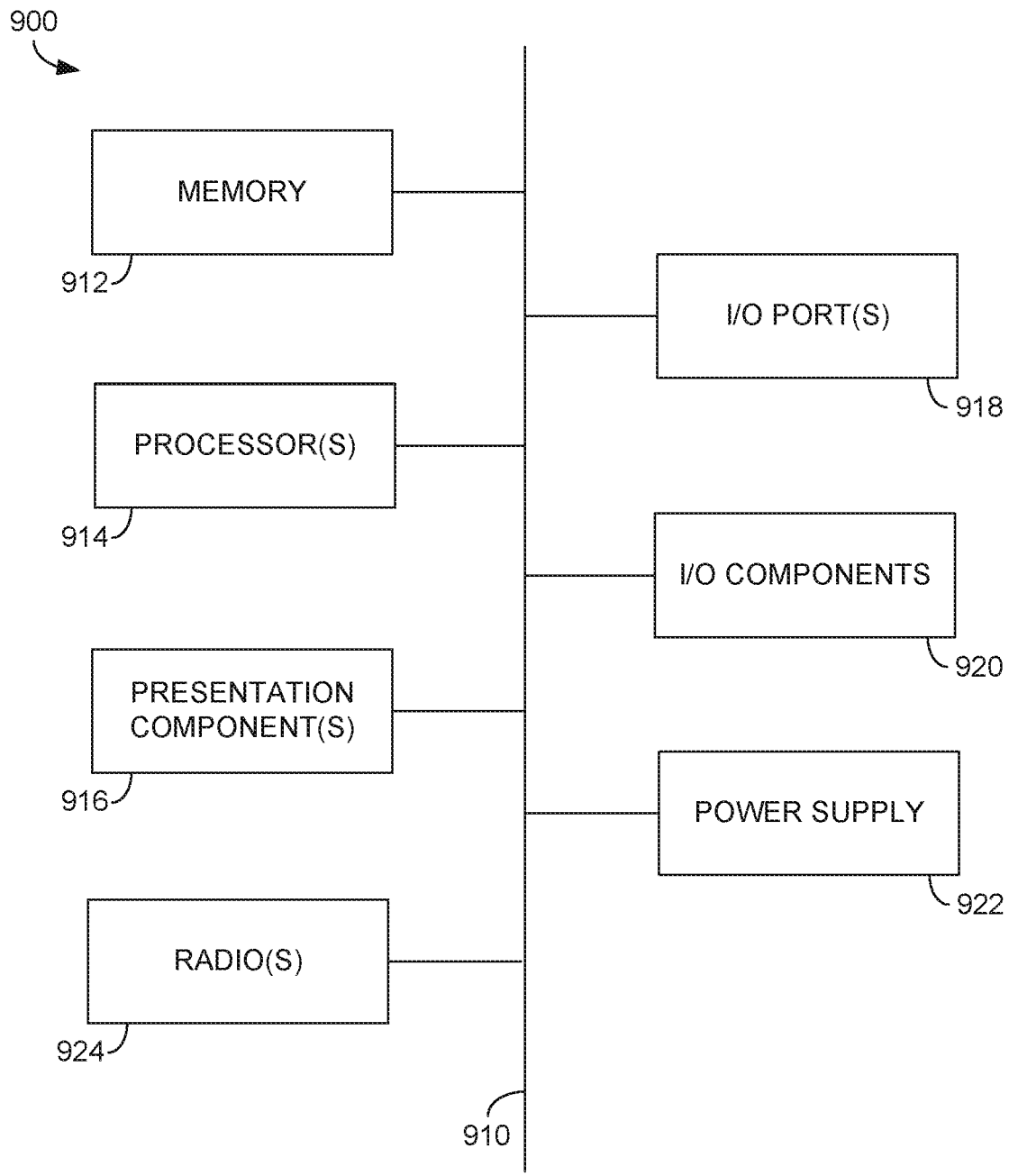

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Example hardware devices include solid-state memory, hard drives, optical-disc drives, etc. Computing system 900 includes one or more processors that read data from various entities such as memory 912 or I/O components 920. Presentation component(s) 916 present data indications to a user or other device. Example presentation components include a display device, speaker, printing component, vibrating component, etc.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, operating environment 100 (or the components of example operating environment 100) include an interface module (or equivalent functionality) for receiving incoming medical data from EHR system(s) 160, a transformation module for transforming the values of input variables referenced in the logistic regression model into intermediate values through dichotomization about a numeric threshold or logical conjunction or sum to totalize individual diagnosis attributions into a composite variable, and a combination module for determining the result of the probability calculation.

Figure 2A:
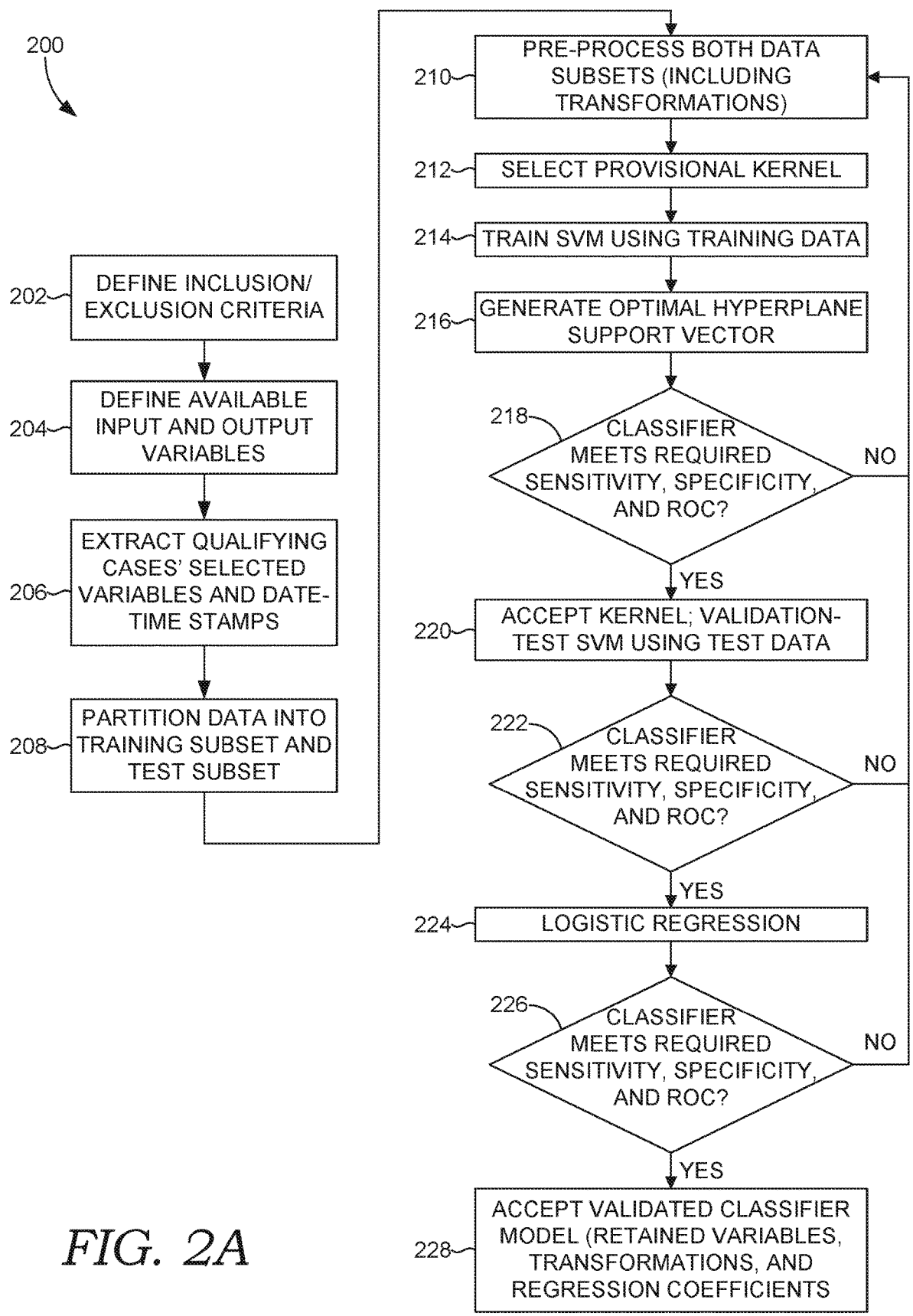
FIG. 2A depicts a flow diagram showing a method for producing and validating a statistical model for accurately predicting a lysosomal storage disorder in accordance with an embodiment of the disclosure.

Turning now to FIG. 2A, a flow diagram is provided that illustrates a method 200 for producing and validating a statistical model for accurately predicting a lysosomal storage disease (or condition) in accordance with an embodiment of the technologies described herein. Initially, inclusion-exclusion criteria are defined, as shown at step (or block) 202, as well as problem specification in terms of available input and output variables, at step 204. Thereafter, as shown at step 206, training data is received. Training data comprises a set of data points having known characteristics. This data may come from research facilities, academic institutions, commercial entities, and/or other public or confidential sources. In the case of the present example embodiment, the data came from an anonymized data warehouse of U.S. hospitals' electronic medical record data. The collection of training data may be accomplished manually or by way of an automated process, such as known electronic data transfer methods. Accordingly, an example embodiment of the learning machine for use in conjunction with the present invention may be implemented in a networked computer environment.

With reference again to step 202, it is known to those practiced in the art that to construct an effective classifier, appropriate inclusion-exclusion criteria are first defined in sufficient detail that the cases acquired for the purpose of classifier design accurately represent the population to which the classifier is intended to be applied. By way of example only and not limitation, in an example embodiment, the inclusion criteria include patients having a lysosomal storage disease condition. Some criteria for case inclusion in classifier development pertain to the dependent variables or 'outcomes' that are the object of the classification.

With reference again to step 204, for the cohort meeting the applicable inclusion-exclusion criteria, database retrieval of extant electronic medical records is performed. This serves to define the available input and output clinical and laboratory variables and characterize the descriptive statistics of each variable and assess the degree of "missingness" of information for each variable. In one embodiment, variables whose values are missing at a greater than 20% rate are excluded from subsequent consideration in classifier construction and development. It should be understood that although database retrieval of electronic medical records is described, any type of patient medical or health record may be utilized within the various embodiments of the present invention (in the context of method 200 or in other contexts of embodiments described herein).

Next, at step 206, information for the qualifying cases for each of the selected variables is extracted from the electronic medical record or other data source, including the date-time stamp for each item. As shown at step 208, the retrieved cases and case information are partitioned into two subsets-a first subset that is to be utilized for classifier construction and training (training data subset), and a second subset that is to be used for classifier validation testing (test data subset). Any of a variety of partitioning methods can be employed such as are well-known to statisticians practiced in the art. Randomized 'bootstrap' sampling without replacement, for example, may be used to insure that the subsets that are generated are not biased with regard to time, source institutions, or other factors. In some embodiments, the partitioning is made into two subsets of equal size (50%-50%). However, there is no requirement that this be the case. The subsets can be of different sizes. In some embodiments, the sample size of each subset is sufficient to achieve a desired 80% or greater statistical power for classification of the cases.

As shown at step 210, statistical pre-processing may be performed, including calculation of mean, median, standard deviation, skewness, and kurtosis for each of the numerical variables and frequency tables for each of the categorical variables. In instances where the statistical distribution of a numerical variable is markedly skewed, then logarithmic or power-law or other transformation of that variable is performed by methods that are well-known to statisticians, so as to produce a distribution for the transformed variable that is symmetrical and more nearly Gaussian in shape than that of the raw variable. The collected training data is optionally pre-processed in order to allow the learning machine to be applied most advantageously toward extraction of the knowledge inherent in the training data. During this preprocessing stage, a variety of different transformations can be performed on the data to enhance its usefulness. Such transformations, examples of which include the addition of expert information, spline conversion, logarithmic or power-law transformations, etc., will be readily apparent to those of skill in the art. However, the preprocessing of interest in an embodiment of the present disclosure is the reduction of dimensionality by way of feature selection.

The resulting dataset is processed with a Support Vector Machine (SVM) algorithm and a provisional kernel is selected, as shown at step 212. Some embodiments of method 200 (and method 201, described in FIG. 2B) utilize computation services 126 (FIG. 1), including R System package gkmSVM. A SVM is a specific type of learning machine that implements a specialized algorithm for providing generalization when estimating a multi-dimensional function from a limited collection of data. The training data subset is used to condition the SVM kernel coefficients and generate a support vector (or hyperplane of the variables) at step 216 that optimally distinguishes the cases according to the dependent variable, which in one embodiment is the outcome of a patient being diagnosed with a lysosomal storage disease. A SVM may be used in estimating classification functions (e.g., pattern-recognition problems) and real-valued functions (e.g., function approximation problems and regression estimation problems). Those skilled in the art should appreciate that SVMs are capable of processing input data having extremely large dimensionality. However, in some embodiments, pre-processing includes the use of feature selection methods to reduce the dimensionality of feature space.

As shown at step 214, the SVM is trained using the pre-processed data from the training data subset. Accordingly, the SVM is trained by adjusting its operating parameters until a desirable training output is achieved. The determination of whether a training output is desirable may be accomplished by comparing the training output to the known characteristics of the training data. A learning machine is considered to be trained when its training output is within a predetermined error threshold from the known characteristics of the training data.

As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge, such as the relation of various clinical and laboratory variables to symptoms of lysosomal storage diseases. Example kernels include polynomial kernels, radial basis function (RBF) classifier kernels, linear kernels, etc. In an alternate embodiment, a customized kernel may be created that is specific to a particular problem or type of data set. The quality of the outputs for each simultaneously trained and tested SVM may be compared using a variety of selectable or weighted metrics to determine whether the kernel chosen performs sufficiently well or whether an alternative kernel achieves superior performance.

At step 218, the resulting classification table is examined by available receiver-operating characteristic (ROC) statistical software, to assess whether the classifier generated by the SVM meets the design requirements established for the predictive model. According to one embodiment, a minimum ROC area-under-the-curve (C-statistic) of 0.80 is required before a model is an acceptable candidate for consideration for logistic regression and subsequent processing and validation. In the event that ROC is lower than the acceptable minimum, then additional iterations of variables selection, pre-processing, kernel generation, and SVM support vector generation are performed (steps 210-218). Alternatively, if ROC is determined to be acceptable at step 218, then the kernel and support vector are accepted and the model is validation-tested, as shown at step 220, using the test data subset that was previously prepared and reserved at step 208. One example ROC for an example embodiment actually constructed using a predictive model generated according to method 200 is illustratively shown in FIG. 4A. Additionally, an example computer program routine for generating the ROC according to method 200 is illustratively provided in FIG. 6.

Figures 4A, 4B:
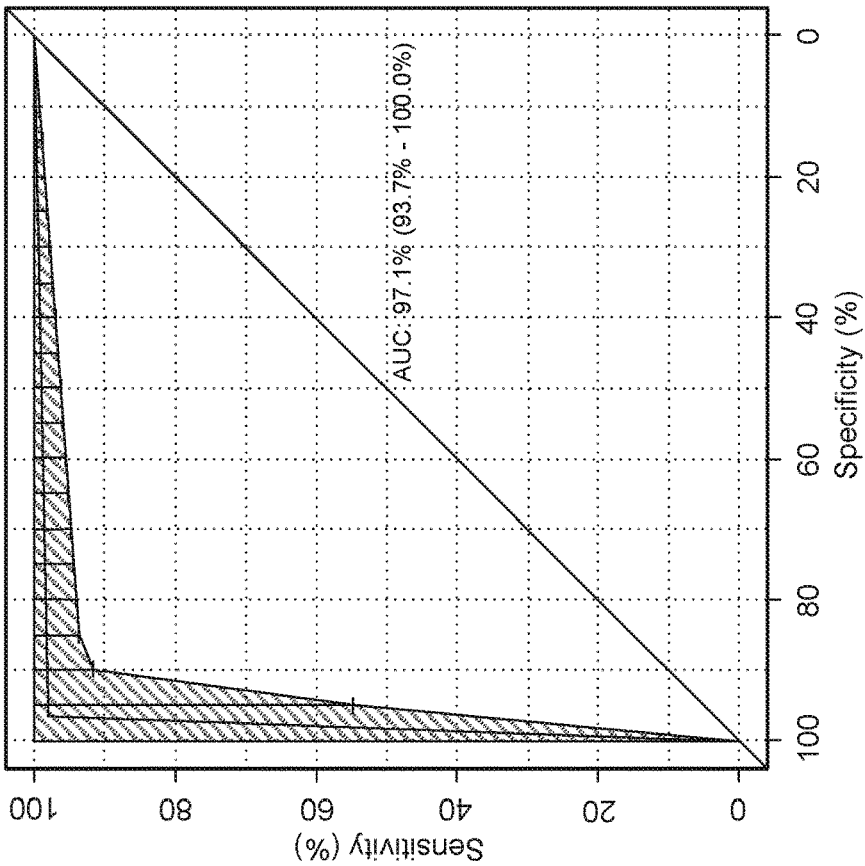
FIGS. 4A and 4B depict aspects of the statistical performance of an example embodiment for predicting a lysosomal storage diseases that is actually reduced to practice, including a receiver operating characteristic (ROC) curve and statistical performance measures.

Based on the post-processed test output, it is determined at steps 222, 224, and 226 whether an optimal minimum was achieved by the SVM and logistic regression. Those skilled in the art should appreciate that a SVM is able to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at step 222, determining whether the optimal minimum has been ascertained may involve comparing the output of a SVM with a historical or predetermined value. One example of the statistical performance, which may be assessed in step 222 is shown in FIG. 4B, which includes statistical performance measurements for the example embodiment actually reduced to practice, described above.

If it is determined that the optimal minimum has not been achieved by the trained SVM, the method moves to step 210, and kernel selection is readjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method is repeated from step 212, where the pre-processed training data is input into the SVM for training purposes. When it is determined at step 222 that the optimal minimum has been achieved, test data is collected similarly as described above. By definition, live data has not been previously evaluated, so that the desired output characteristics that were known with respect to the training data and the test data are not known.

Additional test data is optionally collected in preparation for testing the trained SVM. Test data may be collected from one or more local and/or remote sources. In some embodiments, test data and training data may be collected from the same source(s) at the same time. Thus, test data and training data sets can be divided out of a common data set and stored in a local storage medium for use as different input data sets for a learning machine. Regardless of how the test data is collected, any test data used is pre-processed at step 210 in the same manner as was the training data. As should be apparent to those skilled in the art, a proper test of the learning may only be accomplished by using testing data of the same format as the training data. Then, at step 220, the learning machine is tested using the pre-processed test data, if any. The test output of the learning machine is optionally post-processed in order to determine if the results are desirable. Again, the post processing step involves interpreting the test output into a meaningful form. The meaningful form may be one that is readily understood by a human or one that is compatible with another processor. Regardless, the test output requires post-processing into a form which may be compared to the test data to determine whether the results were desirable. Examples of post-processing steps include but are not limited of the following: optimal categorization determinations, scaling techniques (linear and non-linear), transformations (linear and non-linear), and probability estimations (such as logit or probit equations).

After validation testing has confirmed a vector of variables and transformations that achieves acceptable sensitivity, specificity, and ROC performance, a logistic regression model is calculated, at step 224, utilizing the input variables and transformations that were developed and validated in the previous steps. The generation of the logistic regression model may be done using the training data subset or the entire original dataset or other partitions derived from it, depending on missing data for some variables or other pragmatic factors. Embodiments of method 200 do not depend upon any particular partitioning at this step. Indeed, the sample size available may often dictate what is possible to do, insofar as logistic regression does not tolerate missing data elements. If a decision is made to retain cases that contain missing data in the logistic regression step, then hot-deck or last-value-carry-forward, or other imputation methods may be used, such as are familiar to statisticians.

Finally, the statistical performance of the resulting logistic regression classifier, including its ROC c-statistic, is assessed and, if adequate to the intended purpose, accepted for implementation, as shown at steps 226 and 228. Accepted classifiers may be stored as predictive models utilizing model data and model storage services 128, described in FIG. 1. These predictive models then may be utilized, as described in method 201 (FIG. 2B) for determining presence, identity, and/or severity of a lysosomal storage disorder in a patient.

Utilizing method 200, a set of physiological variables were determined for independent model variables. In particular and in some embodiments, these model variables function as a multi-variable composite biomarker and include one or more of: attribution of arthralgia, attribution of a plurality of the conditions scoliosis or kyphosis, dysostosis, genu valgum, pes cavus, joint contracture, hepatomegaly or splenomegaly, hearing loss/use of hearing aids, recurrent respiratory tract infections or community acquired pneumonia, and sleep apnea/noisy nighttime breathing as a composite variable, elevated C-reactive protein, elevated erythrocyte sedimentation rate, increased red blood cell size distribution width (RDW), elevated aminotransferases, elevated alkaline phosphatase, platelet macrocytosis, and relative decrease in forced expiratory volume and/or forced vital capacity.

Figure 2B:
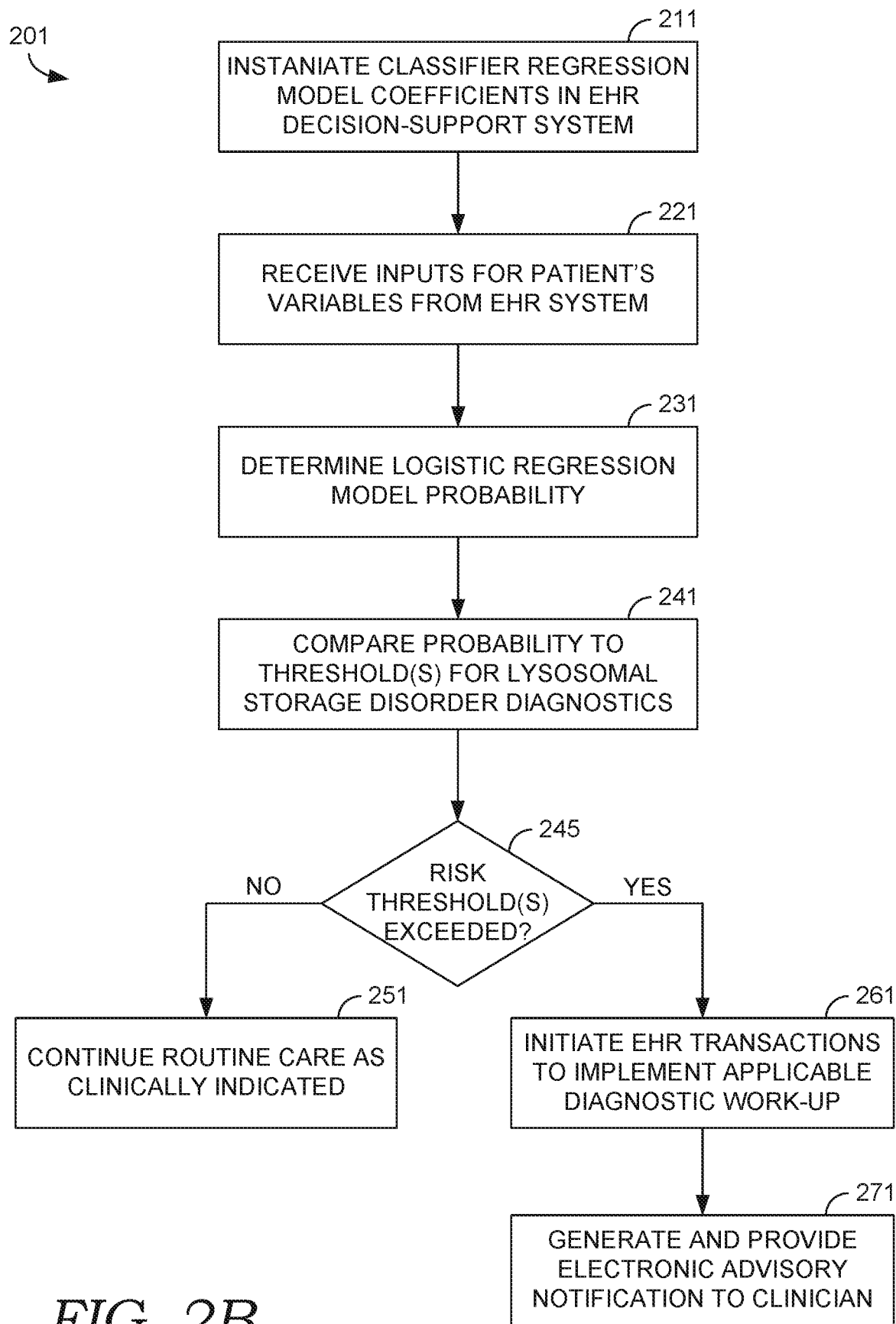
FIG. 2B depicts a flow diagram of an example method for determining presence, identity, and/or severity of a lysosomal storage disorder, such as attenuated MPS-I disease, using a multi-variable logistic regression statistical model, in accordance with an embodiment of the disclosure.

Turning now to FIG. 2B, a flow diagram is provided illustrating a method 201 for determining presence, identity, and/or severity of a lysosomal storage disease or condition using a multi-variable logistic regression statistical model, which may be determined according to method 200 (FIG. 2A). At step 211, instantiate classifier regression model coefficients. Embodiments of step 211 initiate a predictive model having coefficients corresponding to independent model variables. In some embodiments of step 211, the prediction model comprises classifier regression model for classifying likelihood of a patient having a lysosomal storage disease or condition and may be determined according to method 200 (FIG. 2A). In some embodiments, the model is generated using a support vector machine, gradient boosting, or other machine-learning means to reduce the initial dimensionality of the statistical analysis. In some instances, the model (or computer-instructions for instantiating the model when called upon) may be incorporated into a decision-support tool for use by a caregiver, such as a health care professional. Some embodiments integrate with other decision support tools and related tools, such as Cerner Millennium® orders, Discern® Expert CDS, iView®, or similar applications.

At step 221, a patient is identified and EHR information for the patient is accessed. The EHR information may include demographic, diagnostic, and laboratory information about the patient. In particular, at step 221, inputs for variable values corresponding to the independent variables of the classifier model are received from the patient's EHR. At step 231, a logistic regression model probability is determined. In some embodiments, the determined probability may be considered a score denoting the likelihood of the patient's having a lysosomal storage disease or condition. Some embodiments of steps 231 may be performed using computation services 126 (described in connection to FIG. 1A). In particular, aspects of method 201 may be carried out using the example computer program provided in FIG. 5.

At step 241, the determined probability or score is compared to one or more thresholds for lysosomal storage disorder diagnostics. In some embodiments, the threshold(s) may be predetermined, determined empirically, or based on information about the particular patient, caregiver, a treatment context (e.g., the treatment venue, role of the caregiver, insurer, or other clinical conditions or events associated with the patient). In some embodiments, step 241 comprises correlating the magnitude of the composite biomarker with the presence, identity, and/or severity of the disease or condition by comparing the probability against a set of thresholds indicating a presence, identity, and/or severity of a disease or condition associated with the patient. For example, the disease or condition may include a lysosomal storage disease, such attenuated MPS-I disease. In some embodiments, based on the comparison in step 241, one or more risk levels are determined associated with the probability or severity of a lysosomal storage disorder in the patient.

At step 245, based on the comparison to the one or more thresholds, if the threshold(s) are not exceeded, then at step 251 routine care for the patient may be carried out, as clinically indicated. But where the one or more thresholds are satisfied, then method 201 proceeds to step 261 and one or more intervening actions may be invoked. In particular, at step 251, additional diagnostics (such as more expensive or time-consuming testing) may be performed on the patient. In addition or in the alternative, other intervening actions may be performed. These actions may be based on the determined probability or score satisfying the threshold(s) or the specific value of the determined probability or score. For example, such actions may comprise generating and providing an electronic notification at step 271 (such as a message or alert) to the patient or a caregiver regarding the determined presence, identity, and/or severity of the lysosomal storage disorder in the patient, for instance, a message advising a caregiver of the probability of an inherited acid alpha-glucosidase deficiency meriting further diagnostic testing; generating and providing a specific recommendation regarding the treatment or care of the patient (including recommending diagnostics, courses or care, or additional screenings), and/or automatically performing additional actions such as scheduling diagnostic testing, treatments, modification to care plans, or other intervening actions. In one embodiment, an EHR transaction is initiated to implement applicable diagnostic work-up of additional testing procedures for the patient. In some embodiments, an explanatory analysis may be prepared to accompany the model, for significant values and deviations. Further, in some embodiments, the determined score, severity, specific-condition classifications, and/or any recommended actions may be provided via a graphical user interface such as the example user interface shown in FIG. 3, which may be presented via a user/clinician interface 142, described in connection with FIG. 1A.

Example Reduction to Practice

Turning now to FIG. 3, an application graphical user interface 300 is illustratively provided for an example embodiment actually reduced to practice (described below). In some embodiments, example application interface 300 may be embodied as user/clinician interface 142 and/or decision support application 140, described in connection to FIG. 1A. Example application interface 300 may comprise a component of a decision-support tool for predicting a lysosomal storage disease in a human patient, based on a multivariable predictive model, such as a model determined according to method 200.

Example application interface 300 includes a set of model variables 310, which comprise independent model variables for the prediction model. The set of variables (or in some embodiments, a subset of these variables) may be utilized according to a process, such as method 201, to determine likelihood and/or severity of a condition and thus function as a multi-variable composite biomarker. In some embodiments, variables 310 comprise one or more physiological variables, which may be a raw physiological variable or comprises an interpretation of a raw physiological data about the patient, such as whether a patient has two or more comorbid conditions (such as those shown at item 340) or whether the patient has a measurements of serum or blood high-sensitivity C-reactive protein (hsCRP) of greater than 2.8 mg/L. Accordingly, example application interface 300 may be used by a clinician for acquisition and/or display of the values of variables that contribute to the biomarker, and for display of the value of the determined biomarker. In some embodiments, the values for physiological variables 310 may be inputted by a clinician and/or may be automatically determined by the patient's EHR data.

In the example application interface 300, for a patient between 10 and 40 years old, to determine likelihood and severity, each physiological variable corresponds to a coefficient as follows: joint pain or stiffness (ICD-9: 719.4x, 719.5x, ICD-10: M25.xx, M26.xx); two or more of the listed conditions (shown at item 340 of FIG. 3); hsCRP>2.8 mg/L (or elevated C-reactive protein); RDW>16.1 µm (or increased red blood cell size distribution width); RBC sedimentation rate>10 mm/hr (or elevated erythrocyte sedimentation rate); MPV>9.4 fL (platelet macrocytosis); AST>38 U/L (elevated aminotransferases); ALKP>180 U/L (elevated alkaline phosphatase); and FVC % or FEV1%<70% (relative decrease in forced expiratory volume and/or forced vital capacity). Where the physiological variable is not present (including where the interpretation criteria is not satisfied, such as, for instance, where hsCRP is present but not greater than 2.8 mg/L, then the coefficient is set to zero.

Example application interface 300 includes a prediction result 320 indicating the patient's likelihood or severity of having the particular condition and thus warranting further testing. In this example, based on the specific values of the model variables 310, the likelihood is determined as "moderate to high." But if, for example, another variable such as "two or more comorbid conditions" was positive ("Y") instead of negative ("N"), then prediction result 320 would indicate "very high," in this example.

Example application interface 300 also includes items 330, 332, and 336. At item 330, a likelihood score is shown (here "2%"). In one embodiment, the likelihood score may be determined using logistic regression as:

$$\frac{e^{(-7.5+0.71[\text{sum of the model variable coefficients}])}}{1+e^{(-7.5+0.71[\text{sum of the model variable coefficients}])}}$$

In this example, the model coefficients corresponding to the physiological variables (which are zero when the variable is negative or "N") are: [1.38, joint pain or stiffness (ICD-9: 719.4x, 719.5x, ICD-10: M25.xx, M26.xx)]; [1.17, two or more of the listed comorbid conditions]; [0.84, hsCRP>2.8 mg/L]; [0.67, RDW>16.1 µm]; [0.61, RBC sedimentation rate>10 mm/hr]; [0.41, MPV>9.4 fL]; [0.49, AST>38 U/L]; [0.36, ALKP>180 U/L]; and [0.28, FVC % or FEV1%<70%]. Items 332 and 336 comprise an example range corresponding to the likelihood shown at result 320. In this example, item 332 is determined as:

$$\frac{e^{(-.75+0.23[\text{sum of the model variable coefficients}])}}{1+e^{(-.75+0.23[\text{sum of the model variable coefficients}])}}$$

and item 336 is determined as:

$$\frac{e^{(-7.5+1.19[\text{sum of the model variable coefficients}])}}{1+e^{(-7.5+1.19[\text{sum of the model variable coefficients}])}}$$

Reduction to practice and testing was accomplished using a server cluster (computer system 120) running the Linux operating system (operating system 129), the open-source statistical software package R (software services 126), and the R packages kernlab, caret, and gkmSVM, which were utilized for dimensionality reduction by SVM and gradient boosting methods and in particular, using the example computer program routine illustratively depicted in FIG. 5. Initial logistic regression modeling was performed using the glm function in the base R software to produce a regression model that was subjected to a separate validation step.

For the computation of probability or severity of a lysosomal storage disorder: the demographics, laboratory tests, diagnoses, medications, and physical exam records of 1,918 patients having received enzyme-proven diagnosis of MPS-I syndromes in 327 distinct U.S.-based health care institutions between 1 Jan. 2000 and 31 Oct. 2015 were retrieved from a de-identified, secondary-use-consented, EHR-derived, HIPAA-compliant data warehouse (Cerner Health Facts® data warehouse). The retrieval encompassed more than 500 laboratory tests, 23 vital signs and flowsheet observation types, and more than 900 medication types as input variables for classification and predictive analysis. Corresponding records for an age-gender matched set of 2,037 control-patients incident upon the same 327 institutions during the same time interval were also extracted. A support vector machine (SVM) method, such as described in method 200, was used to identify a subset of the input variables, including 6 laboratory tests, that were statistically significantly associated with the diagnosis of the lysosomal storage disease condition (in this specific example actually reduced to practice, attenuated MPS-I syndromes).

To validate the regression model, records of 44 newly-incident attenuated MPS-I disease patients whose care commenced at 27 distinct facilities between 1 Nov. 2015 and 31 Oct. 2016 were retrieved. Corresponding records for 56 age-gender matched control-patients incident upon the same 27 institutions during the same time interval were also extracted. Owing to the small number of patients in the validation cohort, conventional logistic regression was not practical and therefore a Markov Chain Monte Carlo (MCMC) Bayesian method (e.g., metrop function in the mcmc R package) was used to perform confirmatory logistic regression. The MCMC Bayesian logistic regression was successful and produced stable results with 1,000 MCMC iterations. Bayes Information Criterion (BIC) and model regression coefficients did not differ significantly from the initial model. FIGS. 4A and 4B depict aspects of the statistical performance of this example embodiment actually reduced to practice using this clinical dataset, including a ROC curve (FIG. 4A) and statistical performance measures (FIG. 4B).

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present technology. Some example embodiments are provided below:

Embodiment 1: One or more computer-readable storage devices storing computer-useable instructions that, when used by one or more computing devices, cause the one or more computing devices to perform a method comprising: identifying an electronic medical record associated with a human patient; generating a multi-variable logistic regression statistical model capable of calculating a probability of a clinically significant lysosomal storage disease; receiving input data from the medical record for the human patient; determining from the received input data set a multi-variable biomarker based on a set of physiological variables in the received input data comprising at least a plurality of: attribution of arthralgia; attribution of a plurality of conditions from a set of conditions comprising: scoliosis or kyphosis, dysostosis, genu valgum, pes cavus, joint contracture, hepatomegaly or splenomegaly, hearing loss/use of hearing aids, recurrent respiratory tract infections or community acquired pneumonia, and/or sleep apnea/noisy nighttime breathing as a composite variable; elevated C-reactive protein; elevated erythrocyte sedimentation rate; increased red blood cell size distribution width (RDW); elevated aminotransferases; elevated alkaline phosphatase; platelet macrocytosis; and/or relative decrease in forced expiratory volume and/or forced vital capacity; determining a probability of the clinically significant lysosomal storage disease for the human patient based on the multi-variable biomarker and the multi-variable logistic regression statistical model; modifying the electronic medical record according to the determined probability and to include data indicating that the member associated with the medical record is a candidate for receiving additional treatment or diagnostic procedures associated with lysosomal storage disorders; and based on the probability of clinically significant lysosomal storage disease for the human patient, determined from the multi-variable biomarker and the multi-variable logistic regression statistical model, initiating an intervention action, the intervention action comprising one or more of modifying treatment of the patient, ordering additional diagnostics for the patient, scheduling treatment or diagnostics for the patient, and issuing a notification to a caregiver associated with the patient, wherein multi-variable biomarker is used by the multi-variable logistic regression statistical model.

Embodiment 2: Embodiment 1, wherein a plurality of conditions from a set of conditions includes at least two conditions from the set of conditions.

Embodiment 3: Any of Embodiments 1-2, wherein the lysosomal storage disease is attenuated mucopolysaccharidosis Type 1 (acid alpha-iduronidase deficiency).

Embodiment 4: A method of determining the presence, identity, and/or severity of a lysosomal storage disease or condition in an individual, where the disease or condition is associated with the accumulation of abnormal amounts of molecules in lysosome organelles of the individuals' body cells, the method comprising: (a) generating a biomarker as a probability or score emitted by a logistic regression model, wherein the independent variables referenced in the logistic regression model comprise attribution of arthralgia, attribution of a plurality of the conditions scoliosis or kyphosis, dysostosis, genu valgum, pes cavus, joint contracture, hepatomegaly or splenomegaly, hearing loss/use of hearing aids, recurrent respiratory tract infections or community acquired pneumonia, and sleep apnea/noisy nighttime breathing as a composite variable, elevated C-reactive protein, elevated erythrocyte sedimentation rate, increased red blood cell size distribution width (RDW), elevated aminotransferases, elevated alkaline phosphatase, platelet macrocytosis, and relative decrease in forced expiratory volume and/or forced vital capacity; and (b) correlating the magnitude of the biomarker with the presence, identity, and/or severity of the disease or condition for determining the presence, identity, and/or severity of the disease or condition; wherein the disease or condition is a lysosomal storage disease; wherein when the lysosomal storage disease is a lysosomal storage disease; and wherein the lysosomal storage disease is attenuated mucopolysaccharidosis Type 1 (acid alpha-iduronidase deficiency).

Embodiment 5: Embodiment 4, wherein the multi-variable logistic regression statistical model is generated using a support vector machine, gradient boosting, or other machine-learning means to reduce the initial dimensionality of the statistical analysis.

Embodiment 6: Any of Embodiments 4-5, wherein the method further comprises determining one or more risk levels associated with the probability or severity of the lysosomal storage disorder in a human patient.

Embodiment 7: Any of Embodiments 4-6, wherein the method further comprises communicating for presentation to a clinician the one or more risk levels.

Embodiment 8: Any of Embodiments 4-7, wherein the method further includes communicating the electronic medical record to a clinician, where electronic medical record indicates the probability or severity of the lysosomal storage disorder in a human patient.

Embodiment 9: A method for screening for the presence, identity, and/or severity of a lysosomal storage disorder in a human patient, comprising: generating a multi-variable logistic regression statistical model capable of calculating a probability or severity of said lysosomal storage disorder using a plurality of variables; receiving an input data set for a human patient based on laboratory test results for the patient, the data set including a time associated with the test results, the test results determined from measurements that may be received at multiple measurement-session times; determining a probability or severity of said lysosomal storage disorder based on the input data set and the multi-variable logistic regression statistical model; modifying an electronic medical record associated with the patient according to the determined probability indicating that the patient is or is not a candidate for additional diagnostic testing and treatment; and based on the probability or severity of said lysosomal storage disorder for the human patient determined from the input data set and the multi-variable logistic regression statistical model, initiating an intervention, the intervention comprising undertaking additional diagnostic or prognostic enzymatic or genetic testing directed to one or more specific lysosomal storage disorders, wherein the independent variables of the model include at least a plurality of: attribution of arthralgia; attribution of a plurality of conditions from a set of conditions comprising: scoliosis or kyphosis, dysostosis, genu valgum, pes cavus, joint contracture, hepatomegaly or splenomegaly, hearing loss/use of hearing aids, recurrent respiratory tract infections or community acquired pneumonia, and sleep apnea/noisy nighttime breathing as a composite variable; elevated C-reactive protein; elevated erythrocyte sedimentation rate; increased red blood cell size distribution width (RDW); elevated aminotransferases; elevated alkaline phosphatase; platelet macrocytosis; and relative decrease in forced expiratory volume and/or forced vital capacity.

Embodiment 10: Embodiment 9, wherein the multi-variable logistic regression statistical model is generated using a support vector machine, gradient boosting, or other machine-learning means to reduce the initial dimensionality of the statistical analysis.

Embodiment 11: Any of Embodiments 9-10, wherein the method further comprises determining one or more risk levels associated with the probability or severity of said lysosomal storage disorder.

Embodiment 12: Any of Embodiments 9-11, wherein the method further comprises communicating for presentation to a clinician the one or more risk levels.

Embodiment 13: Any of Embodiments 9-12, further comprising communicating the electronic medical record to a clinician, where electronic medical record indicates the probability or severity of said lysosomal storage disorder.

Embodiment 14: Embodiment 1, wherein the probability comprises a multi-variable predictive score calculated using the multi-variable logistic regression statistical model, therein the multi-variable logistic regression statistical model is capable of calculating a probability or severity of the lysosomal storage disorder.

Embodiment 15: Any of Embodiments 1 and 14, wherein the multi-variable logistic regression statistical model employs a multi-variable support vector machine, gradient boosting, or other machine-learning means to reduce the initial dimensionality of the statistical analysis.

Embodiment 16: Any of Embodiments 1 and 14-15, wherein one or more risk levels are identified based on the probability or severity of the lysosomal storage disorder.

Embodiment 17: Any of Embodiments 1 and 14-16, wherein the one or more risk levels are presented to a clinician via an electronic medical record software system or device.

Embodiment 18: Any of Embodiments 1 and 14-17, wherein the intervention is identified based on the one or more risk levels.

Embodiment 19: A method of determining the presence, identity, and/or severity of a lysosomal storage disease or condition in an individual, implemented in an electronic medical software system, the method comprising: identifying an electronic medical record associated with each member of a set of members of the population who exhibit an above-threshold value of a multi-variable predictive score, the value of the multi-variable predictive score being calculated from a multi-variable logistic regression statistical model and a plurality of variables determined at least in part from laboratory test results from a single set of measurements measured at a known time following birth, and including the known time following birth of the measured test results; and modifying the electronic medical record with data indicating that the member associated with the medical record is a candidate for intervention; and based on the value of the multivariable predictive score, initiating a diagnostic or therapeutic intervention.

Embodiment 20: Embodiment 19, wherein the multi-variable predictive score is calculated using the multi-variable logistic regression statistical model, therein the multi-variable logistic regression statistical model is capable of calculating a probability or severity of said lysosomal storage disorder.

Embodiment 21: Any of Embodiments 19-20, wherein the multi-variable logistic regression statistical model employs a multi-variable support vector machine, gradient boosting, or other machine-learning means to reduce the initial dimensionality of the statistical analysis.

Embodiment 22: Any of Embodiments 19-21, wherein one or more risk levels are identified based on the probability or severity of the lysosomal storage disorder.

Embodiment 23: Any of Embodiments 19-22, wherein the one or more risk levels are presented to a clinician via an electronic medical record software system or device.

Embodiment 24: Any of Embodiments 19-23, wherein the intervention is identified based on the one or more risk levels.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system operative to provide a decision support tool for diagnosing a lysosomal storage disease, the system having one or more processors configured to cause a plurality of operations comprising:
generating a lysosomal storage prediction model, wherein generating the lysosomal storage prediction model comprises:
defining inclusion-exclusion criteria, wherein the inclusion-exclusion criteria include a lysosomal storage disease;

retrieving an electronic health record (EHR) based on the inclusion-exclusion criteria;
extracting from the EHR health information for a biomarker pattern, wherein the biomarker pattern is indicative of the lysosomal storage disease;
determining a provisional kernel;
based on the provisional kernel, training a Support Vector Machine (SVM) algorithm using at least a portion of the health information for the biomarker pattern; and
determining the trained SVM is a candidate for use as the lysosomal storage prediction model;
identifying a candidate EHR;
receiving variable inputs from the candidate EHR based on the biomarker pattern;
utilizing the lysosomal storage prediction model to predict a probability of the lysosomal storage disease; and
based on the probability of the lysosomal storage disease, initiating an intervening action that includes at least a notification of the lysosomal storage disease and automatically triggering one or more EHR transactions to initiate diagnostic testing procedures.

2. The system of claim 1, wherein the biomarker pattern includes one or more of: arthralgia; at least two of: scoliosis, kyphosis, dysostosis, genu valgum, pes cavus, joint contracture, hepatomegaly, splenomegaly, hearing loss, use of hearing aids, recurrent respiratory tract infections, community acquired pneumonia, sleep apnea, and noisy nighttime breathing; and at least one of: elevated C-reactive protein; elevated erythrocyte sedimentation rate; increased red blood cell size distribution width (RDW); elevated aminotransferases; elevated alkaline phosphatase; platelet macrocytosis; decrease in forced expiratory volume; and decrease in forced vital capacity.

3. The system of claim 1, wherein the lysosomal storage disease is attenuated mucopolysaccharidosis Type 1.

4. The system of claim 1, further comprising determining a risk level associated with the probability of the lysosomal storage disease, the risk level included in the notification.

5. The system of claim 1, wherein the provisional kernel is determined based on prior performance knowledge of various clinical and laboratory variables to symptoms of the lysosomal storage disease.

6. The system of claim 1, wherein the trained SVM is determined to be a candidate based on a receiver-operating characteristic (ROC) curve.

7. The system of claim 6, wherein the trained SVM is determined to be the candidate for use as the lysosomal storage prediction model when an area under the ROC curve is equal to or greater than 0.80.

8. The system of claim 1, further including validating the lysosomal storage prediction model using a subset of the health information for the biomarker pattern, wherein the subset is not used to train the SVM algorithm.

9. The system of claim 1, further comprising determining the trained SVM achieves an optimum minimum error.

10. The system of claim 9, wherein the provisional kernel is determined based on the optimum minimum error.

11. A computer-implemented method for diagnosing a lysosomal storage disease, the method comprising:
generating a lysosomal storage prediction model, wherein the lysosomal storage prediction model is generated from training a Support Vector Machine (SVM) based on health information for a biomarker pattern indicative of the lysosomal storage disease, the heath information extracted from an electronic health record (EHR);
identifying a candidate EHR;
receiving variable inputs from the candidate EHR based on the biomarker pattern;
utilizing the lysosomal storage prediction model to predict a probability of the lysosomal storage disease; and
based on the probability of the lysosomal storage disease, initiating an intervening action that includes at least a notification of the lysosomal storage disease and automatically triggering one or more EHR transactions to initiate diagnostic testing procedures.

12. The computer-implemented method of claim 11, wherein the biomarker pattern includes one or more of: arthralgia; at least two of: scoliosis, kyphosis, dysostosis, genu valgum, pes cavus, joint contracture, hepatomegaly, splenomegaly, hearing loss, use of hearing aids, recurrent respiratory tract infections, community acquired pneumonia, sleep apnea, and noisy nighttime breathing; and at least one of: elevated C-reactive protein; elevated erythrocyte sedimentation rate; increased red blood cell size distribution width (RDW); elevated aminotransferases; elevated alkaline phosphatase; platelet macrocytosis; decrease in forced expiratory volume; and decrease in forced vital capacity.

13. The computer-implemented method of claim 11, further comprising determining a risk level associated with the probability of the lysosomal storage disease, the risk level included in the notification.

14. The computer-implemented method of claim 11, wherein a provisional kernel is determined based on prior performance knowledge of clinical and laboratory variables to symptoms of the lysosomal storage disease.

15. The computer-implemented method of claim 11, wherein the trained SVM is determined to be a candidate based on a receiver-operating characteristic (ROC) curve, and wherein the trained SVM is determined to be the candidate for use as the lysosomal storage prediction model when an area under the ROC curve is equal to or greater than 0.80.

16. One or more non-transitory media having instructions that, when executed by one or more processors, cause a plurality of operations, the operations comprising:
generating a lysosomal storage prediction model, wherein the lysosomal storage prediction model is generated from training a Support Vector Machine (SVM) based on health information for a biomarker pattern indicative of a lysosomal storage disease, the heath information extracted from an electronic health record (EHR);
identifying a candidate EHR;
receiving variable inputs from the candidate EHR based on the biomarker pattern;
utilizing the lysosomal storage prediction model, predict a probability of the lysosomal storage disease; and
based on the probability of the lysosomal storage disease, initiating an intervening action and automatically triggering one or more EHR transactions to initiate diagnostic testing procedures.

17. The one or more non-transitory media of claim 16, wherein the biomarker pattern includes one or more of: arthralgia; at least two of: scoliosis, kyphosis, dysostosis, genu valgum, pes cavus, joint contracture, hepatomegaly, splenomegaly, hearing loss, use of hearing aids, recurrent respiratory tract infections, community acquired pneumonia, sleep apnea, and noisy nighttime breathing; and at least one of: elevated C-reactive protein; elevated erythrocyte sedimentation rate; increased red blood cell size distribution width (RDW); elevated aminotransferases; elevated alkaline phosphatase; platelet macrocytosis; decrease in forced expiratory volume; and decrease in forced vital capacity.

18. The one or more non-transitory media of claim 16, wherein the intervening action includes at least one of generating a notification based on the probability of the lysosomal storage disease, generating a treatment recommendation for the lysosomal storage disease, scheduling diagnostic testing or treatments for the lysosomal storage disease, or modifying a care plan associated with the lysosomal storage disease.

19. The one or more non-transitory media of claim 16, further comprising determining a risk level associated with the probability of the lysosomal storage disease.

20. The one or more non-transitory media of claim 16, wherein the lysosomal storage disease is attenuated mucopolysaccharidosis Type 1.

21. The one or more non-transitory media of claim 16, wherein the operations further comprise updating the lysosomal storage prediction model based on information associated with instances of information selected from a group comprising additional information for one or more biomarker patterns indicative of the lysosomal storage disease and additional heath information extracted from one or more EHRs.

22. The one or more non-transitory media of claim 16, wherein generating the lysosomal storage prediction model is based at least in part on a training process selected from a group comprising supervised machine learning, reinforcement machine learning, and unsupervised machine learning.

* * * * *